United States Patent [19]

Hughes et al.

[11] 4,201,210
[45] May 6, 1980

[54] VETERINARY OCULAR RING DEVICE FOR SUSTAINED DRUG RELEASE

[75] Inventors: David E. Hughes; George W. Pugh, Jr., both of Ames, Iowa

[73] Assignee: The United States of America as represented by the Secretary of Agriculture, Washington, D.C.

[21] Appl. No.: 855,495

[22] Filed: Nov. 28, 1977

Related U.S. Application Data

[63] Continuation of Ser. No. 698,632, Jun. 22, 1976, abandoned.

[51] Int. Cl.² .............................................. A61M 7/00
[52] U.S. Cl. ..................................... 128/260; 424/22; 424/28
[58] Field of Search .................... 128/260; 424/14, 22, 424/28

[56] References Cited

U.S. PATENT DOCUMENTS

| | | | |
|---|---|---|---|
| 3,064,643 | 11/1962 | Dixon | 128/76.5 |
| 3,302,646 | 2/1967 | Behney | 128/260 |
| 3,416,530 | 12/1968 | Ness | 128/260 |
| 3,520,277 | 2/1976 | Higuchi et al. | 128/260 |
| 3,710,796 | 1/1973 | Neefe | 128/260 |
| 3,786,812 | 1/1974 | Neefe | 128/260 |
| 3,807,398 | 4/1974 | Grucza | 128/260 |
| 3,949,750 | 4/1976 | Freeman | 128/260 |
| 3,961,628 | 6/1976 | Arnold | 128/260 |
| 3,986,510 | 10/1976 | Higuchi et al. | 128/260 |
| 3,995,635 | 12/1976 | Higuchi et al. | 128/260 |

FOREIGN PATENT DOCUMENTS

| | | |
|---|---|---|
| 911836 | 10/1972 | Canada . |
| 1003914 | 3/1957 | Fed. Rep. of Germany . |
| 2441191 | 3/1975 | Fed. Rep. of Germany . |
| 1549286 | 12/1968 | France . |
| 43-15518 | 6/1968 | Japan . |
| 6709248 | 1/1969 | Netherlands . |

OTHER PUBLICATIONS

Hughes et al., Vet Bull., 46, No. 504, Jan. 1976, Infectious Bovine Keratoconjunctivitis.
Lonsdale, Chemtech, Nov. 1975, pp. 668–674, Controlled Delivery–An Emerging Use for Membranes.
Shell American Druggist, Sep. 1974, pp. 44–45, A New Method of Administering Ophthalmic Drugs.
Lerman et al., Canad. J. Ophthal., 8:114–118, 1973, Prolonged Release Hydrocortisone Therapy.
Morgan Industrial Medicine, 40, Sep. 1971, A New Drug Delivery System for the Eye.

*Primary Examiner*—John D. Yasko
*Attorney, Agent, or Firm*—M. Howard Silverstein; David G. McConnell; Curtis P. Ribando

[57] ABSTRACT

A novel ring-shaped device inserted into the conjunctival sac of an animal eye exhibits potential for prolonged release of therapeutic drugs to the eye region. Its prolonged retention properties render it suitable for use in the extended treatment of obstinate ocular infections, such as infectious bovine keratoconjunctivitis in cattle.

16 Claims, 4 Drawing Figures

VETERINARY OCULAR RING DEVICE FOR SUSTAINED DRUG RELEASE

This is a continuation of application Ser. No. 698,632 filed June 22, 1976, now abandoned.

BACKGROUND OF THE INVENTION

The field of this invention relates to prolonged release, ocular treatment for veterinary uses. It particularly pertains to the treatment of obstinate ocular infections, such as infectious bovine keratoconjunctivitis (IBK), or pinkeye, in cattle.

Known methods of treatment for infections such as IBK range from topical application of drops, ointments, or sprays to parenteral injection of a variety of antibiotics and sulfonamides.

A disadvantage of such treatment methods has been the difficulty of both obtaining and maintaining a therapeutic concentration of the drug in the tears and the affected tissues. One approach to the problem was reported by G. E. Hawley ("A New Treatment for Infectious Keratitis," North Am. Vet. 35: 507–509, July 1954). The tested procedure utilized an eye pellet that provided for a residual therapeutic concentration of terramycin in the tears for 31 hr.

A new form of prolonged release medication has been reported for use in treating glaucoma in humans (S. Lerman, "Prolonged Release Medication in the Treatment of Eye Disease," Isr. J. Med. Sci. 8: 1402–1405, Aug.-Sept. 1972). This device consists of an erodable matrix incorporating pilocarpine into a polymer so that the drug is released as the matrix dissolves. The structure of the device is relatively small as compared to the eye and is generally in the shape of a thin elliptical, solid body. It is designed for insertion into the ventral fornix of the conjunctival sac. However, in insertion tests performed on bovine eyes, the device floated in the tear film and frequently emerged from beneath the eyelid. Moreover, the nictitating membrane (third eyelid), which is not present in the human eye, caused the migration of the unit medially and propelled it onto the skin surface at the medial canthus. The units were retained for periods ranging from 5 min. to 2 hr.

SUMMARY OF THE INVENTION

The instant invention provides an improvement in the art for ocular treatment of animals. A novel ring-shaped device inserted into the conjunctival sac exhibits potential for prolonged release of therapeutic drugs to the eye. The improved position retention properties imparted by the design of the device renders it suitable for use in the extended treatment of obstinate ocular infections, such as infectious bovine keratoconjunctivitis and Moraxella carrier states in cattle.

DETAILED DESCRIPTION OF THE PREFERRED EMBODIMENTS

The instant invention developed as a result of a study to determine the feasibility of designing prolonged release ocular devices for use in the treatment of infectious bovine keratoconjunctivitis (IBK). The approach considered the anatomic structures of the bovine eye that might affect the retention of the devices. The relationship of these structures to the size and shape of a device needed to achieve prolonged retention in the bovine eye were primary considerations.

The invention is not limited to treatment of bovine animals but is applicable to any animal having a similar eye structure, inclusive of horses, dogs, sheep, and others. Moreover, the invention can be used for treatment of any eye disorder which is normally treatable by topical application of a therapeutic agent.

Figure 1:
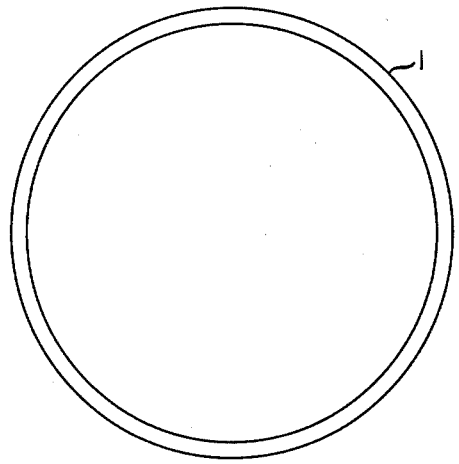
FIG. 1 is a plane view of the ring-shaped device of the instant invention.

The novel apparatus is a substantially ring-shaped device 1 as depicted in FIG. 1. It may be solid or hollow and have any outer cross-sectional shape inclusive or circular, elliptical, rectangular, etc. The smoother shapes, such as the circular and elliptical cross-sections, are preferred. The ring should be sufficiently pliable to permit conformation to the eye structure but of sufficient rigidity to substantially maintain its basic shape.

Figure 2:
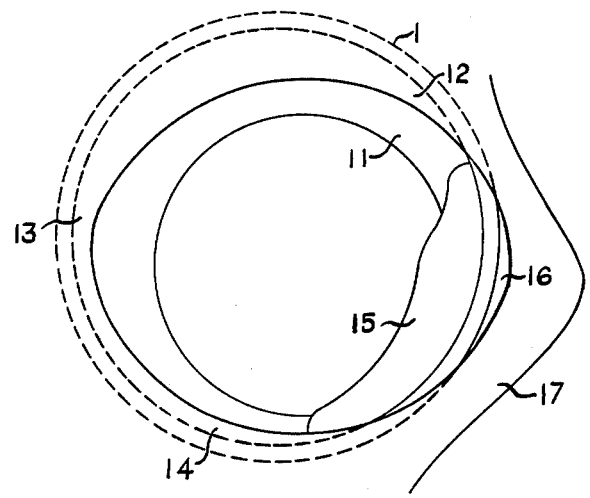
FIG. 2 shows the position of the device of FIG. 1 in a plane view relative to the eyeball and adnexa.
Figure 3:
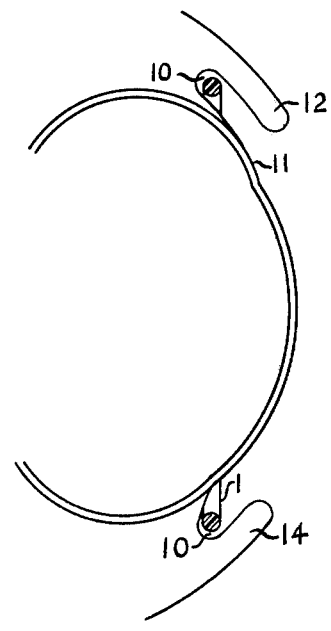
FIG. 3 shows the position of the device of FIG. 1 in a saggital section relative to the eyeball and adnexa.

As depicted in FIGS. 2 and 3, the size of the device is designed to have a circumference smaller than that of the conjunctival sac 10, but larger than that of the eye's globe 11. When inserted, the top part of the ring is fitted in the conjunctival sac beneath the dorsal lid 12. The lateral part rests in the lateral fornix 13 of the sac, and the lower part in the conjunctival sac beneath the ventral lid 14. The medial section of the ring is positioned on the outer surface of the nictitating membrane 15 where it remains visible in the medial canthus 16.

The specific composition from which the novel ring-shaped device is constructed does not constitute part of the invention. However, it is envisioned that it may be formed from an erodable matrix incorporating a treatment drug as in the devices reported by Lerman, supra.

The therapeutic agents or drugs which can be used in conjunction with the instant invention include all those which are intended for topical application to the eye. Exemplary of these are antibiotics such as tetracycline, which is useful in the treatment of IBK in cattle.

Figure 4:
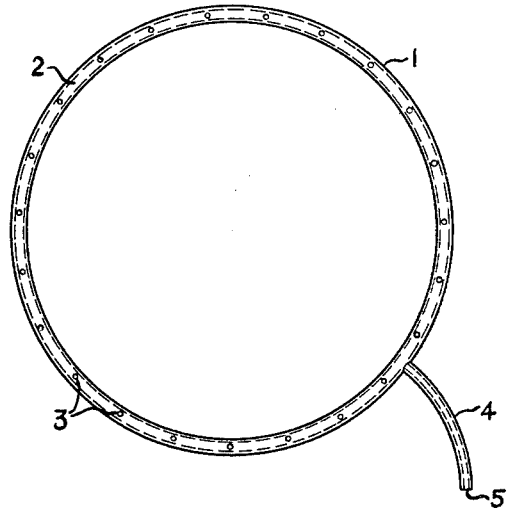
FIG. 4 is a plane view of an alternate embodiment of the ring-shaped device of FIG. 1.

As an alternate embodiment, the device 1 can be constructed of an inert tubing material such as polyvinyl tubing. As shown in FIG. 4, the hollow of the tubing serves as a reservoir 2 for storing the therapeutic agent. The tubing is also provided with a plurality of minute holes 3 for distributing the agent from the reservoir 2 to the surface of the eye over a prolonged period. It is preferably provided with an appendage 4 having an inlet 5 for refilling the reservoir with the drug. The appendage may be sewn onto the skin 17 in the area of the medial canthus 16 in order to assist in retaining the ring in position.

The invention is further illustrated by the following examples.

EXAMPLE 1

Sustained release devices designed for use in human eyes, supplied by Ocusert, Alza Corporation, Palo Alto, Calif., were tested in the eyes of healthy dairy-type calves, 4 to 10 mo. of age. The devices were placed in the ventral fornix of the conjunctival sac with thumb forceps after eversion of the ventral lid. They were easily inserted and caused no obvious discomfort beyond an increased tear pool and a tendency to blink. They floated on the tear film, emerged from beneath the lids, and sometimes were returned beneath the lid by blinking. The nictitating membrane caused the migration of the unit medially and propelled it onto the skin surface at the medial canthus. The units were retained for periods ranging from 5 min. to 2 hr.

EXAMPLE 2

Experimental rings of various circumference dimensions were fabricated with intramedic polyethylene tubing, Catalogue No. 160, supplied by Clay Adams, Inc. Parsippany, N.J. The inside diameter of the tubing measured 1.14 mm. and the outside diameter was 1.58 mm. The ends of the tubing were joined with short sections of connector tubing on the inside.

The ring devices were tested in the eyes of healthy dairy-type calves, 4 to 10 mo. of age. The devices were inserted by holding the eyelids open while one side of the ring was directed into the lateral fornix of the conjunctival sac. The rest of the ring was then directed under the lids and finally onto the outer surface of the nictitating membrane where it remained visible in the medial canthus.

The polyethylene tubing had a tendency to bend sharply during insertion and form a permanent crease. When this happened to a ring, the circular shape was broken and it was more readily ejected.

Local reaction to the ring devices was minimal and ranged from an increased tear pool initially to an increased mucous secretion after prolonged retention. Scoring of ocular irritation, according to the Draize technique[1], was 0 for all four factors on all cattle in the experiment. Though a few areas of chemosis were seen at certain pressure points of the conjunctivas after long retention, the membranes were not ulcerated and the corneas remained normal.

[1] A description of the test, including a grading and scoring system, is given in "Appraisal of the Safety of Foods, Drugs, and Cosmetics" published in 1959 by the Association of Food and Drug Officials of the United States. This test has been modified to satisfy one of the criteria [in Sec. 191.1 (g) (3)] for determining whether or not a substance is an eye irritant under the Federal Hazardous Substances Labeling Act. The modified test appears as Sec. 191.12.

The retention times of the ring devices are set forth in Table I below.

EXAMPLE 3

Experimental rings of various circumference dimensions were fabricated from Medical grade polyvinyl tubing, supplied by Becton-Dickinson and Company, Rutherford, N.J. Two sizes of polyvinyl tubing were used:

A 0.711 inside diameter    0.914 outside diameter
B 1.12 inside diameter     1.42 outside diameter The ends of the tubing materials were brought into abutment and connected to form the ring devices as described in Table II below.

The ring devices were inserted into the eyes of healthy dairy-type calves, 4 to 10 mo. of age, as described in Example 2. As with the polyethylene devices, little local reaction was observed.

The retention times of the ring devices are set forth in Table III below.

The results of the examples indicate that the ring devices are uniquely suited for use in the animal eye having a nictitating membrane (third eyelid), such as the bovine eye. In addition to the long retention time (up to 19 da.) in the conjunctival sac, they caused only slight adverse reactions and were inserted with ease. Best results are obtained if the ring fits over the globe of the eye and rests deeply into the fornix except medially at the third eyelid where it is retained adjacent to the medial commisure. If the ring is too large, the pressure from the conjunctival sac tends to force the ring out. If it is too small, the ring rides on the globe and its position is unstable. For the cattle tested in the above examples, operable ring circumferences ranged from 135–140 cm. with the optimum size being 139 cm. However, it is to be understood that the actual operable ring size varies with both the animal species and the individual animal within each species. Generally, it is a function of the size of the conjunctival sac.

It is to be understood that the foregoing detailed description is given by way of illustration and that modifications and variations may be made therein without departing from the spirit and scope of the invention.

Table I

| Ring type | Ring circumference, mm. | Number tested | Number ejected within 2 da. | Number retained 2 da. or longer (No. of da.) |
|---|---|---|---|---|
| PE 1 | 150 | 1 | 1 | 0 |
| PE 2 | 140 | 4 | 3 | 1 (19) |
| PE 3 | 139 | 4 | 0 | 1 (2), 1 (6), 1 (7), 1 (16) |
| PE 4 | 135 | 4 | 2 | 1 (11), 1 (13) |
| PE 5 | 126 | 2 | 2 | 0 |

Table II

| Ring type | Polyvinyl ring material | Polyvinyl ring connector | Ring circumference, mm. |
|---|---|---|---|
| PV 1 | B | A (12 mm. inside support) | 139 |
| PV 2 | A | B (12 mm. outside support with copper wire inside support) | 139 |
| PV 3 | A | B (12 mm. outside support) | 139 |

Table III

| Ring type | Ring circumference, mm. | Number tested | Number ejected within 1 da. | Number retained 1 da. or longer (No. of da.) |
|---|---|---|---|---|
| PV 1 | 139 | 3 | 1 | 2 (14) |
| PV 2 | 139 | 2 | 2 | 0 |
| PV 3 | 139 | 2 | 1 | 1 (removed after 1 da.) |

We claim:

1. A method for releasing over a prolonged period of time a therapeutic agent into the region of an eye of an animal comprising inserting into the conjunctival sac of said eye a substantially ring-shaped device releasably containing said therapeutic agent, and releasing said agent into said eye region over a prolonged period.

2. The method of claim 1, wherein said inserted device is sufficiently pliable in all dimensions to permit conformation to the shape of said conjunctival sac.

3. The method of claim 1, wherein said inserted device surrounds the globe of the eye.

4. The method of claim 1, wherein said animal is a bovine.

5. The method of claim 1, wherein said therapeutic agent is an antibiotic.

6. The method of claim 1, wherein said ring-shaped device comprises an erodable matrix having said therapeutic agent releasably contained therein, and said releasing step is effected by the degradation of said matrix.

7. The method of claim 1, wherein said therapeutic agent is contained within a reservoir internal to said ring-shaped device, and said agent is released over a prolonged period through a plurality of holes from said reservoir to said eye region.

8. An apparatus adapted for insertion into the conjunctival sac of the eye of an animal surrounding the globe of said eye comprising a ring-shaped member having means associated therewith for the prolonged release of a therapeutic agent into the region of said eye.

9. The apparatus defined by claim 8 wherein said prolonged release means comprises an erodable matrix.

10. The apparatus defined by claim 8 wherein said prolonged release means comprises an internal reservoir cavity in said ring-shaped member for holding said therapeutic agent and a plurality of holes communicating with said cavity and the exterior of said member for releasing said agent into said eye region.

11. The apparatus defined by claim 10 further comprising a hollow tubular appendage affixed to said member and in communication with said internal cavity adapted for filling said cavity with said agent.

12. A method for releasing over a prolonged period of time a therapeutic agent into the region of an eye of an animal having an eye structure inclusive of a nictitating membrane, comprising inserting into the conjunctival sac of said eye, surrounding the globe of said eye, and positioning onto the outer surface of said nictitating membrane a substantially ring-shaped device releasably containing said therapeutic agent, and releasing said agent into said eye region over a prolonged period.

13. An apparatus adapted for insertion into the conjunctival sac of the eye of an animal and further adapted for surrounding the globe of said eye and for positioning onto the outer surface of the nictitating membrane comprising a ring-shaped member having means associated therewith for the prolonged release of a therapeutic agent into the region of said eye.

14. In a non-corneal, drug dispensing ocular insert comprising a flexible body containing a drug for application to the eyeball to dispense said drug to the eye over a prolonged period of time, the improvement comprising a means for permitting facile insertion into and comfortable retention within the eye, and concomitantly preventing the expulsion of the insert therefrom, wherein said flexible body comprises an annular ring that is sized relative to the eye so it can be placed about the eyeball and in contact therewith, completely posterior to the sulcus sclerae and within the upper and lower cul-de-sacs, the width of the ring being such that the ring is virtually invisible in the palpebral fissure when the eyelids are open.

15. The ocular insert as defined by claim 14, containing an ophthalmic drug.

16. The ocular insert as defined in claim 14, wherein said width is about 1 to 12 mm.

* * * * *